(12) United States Patent
McWherter

(10) Patent No.: US 11,172,816 B2
(45) Date of Patent: *Nov. 16, 2021

(54) DIGITAL 3D INFRARED SLIT LAMP WITH PUPIL MEASUREMENT

(71) Applicant: Ian W McWherter, Louisville, KY (US)

(72) Inventor: Ian W McWherter, Louisville, KY (US)

(\*) Notice: Subject to any disclaimer, the term of this patent is extended or adjusted under 35 U.S.C. 154(b) by 0 days.

This patent is subject to a terminal disclaimer.

(21) Appl. No.: 16/792,833

(22) Filed: Feb. 17, 2020

(65) Prior Publication Data

US 2020/0178796 A1 Jun. 11, 2020

Related U.S. Application Data

(62) Division of application No. 15/981,930, filed on May 17, 2018, now Pat. No. 10,820,797.

(60) Provisional application No. 62/636,867, filed on Mar. 1, 2018.

(51) Int. Cl.
| | |
|---|---|
| *A61B 3/135* | (2006.01) |
| *A61B 3/15* | (2006.01) |
| *A61B 3/11* | (2006.01) |
| *A61B 3/12* | (2006.01) |
| *A61B 3/107* | (2006.01) |

(52) U.S. Cl.
CPC .............. *A61B 3/135* (2013.01); *A61B 3/112* (2013.01); *A61B 3/15* (2013.01); *A61B 3/107* (2013.01); *A61B 3/12* (2013.01)

(58) Field of Classification Search
CPC ............ A61B 3/10; A61B 3/103; A61B 3/107; A61B 3/1015; A61B 3/11; A61B 3/112; A61B 3/113; A61B 3/12; A61B 3/14; A61B 3/135; A61B 3/15; A61B 3/00; A61B 1/06; A61B 1/0684; A61B 1/0653; A61B 1/227
USPC ....... 351/205, 206, 209–212, 214, 221, 243, 351/246
See application file for complete search history.

(56) References Cited

U.S. PATENT DOCUMENTS

| | | | |
|---|---|---|---|
| 5,841,509 A * | 11/1998 | Harooni ................. | A61B 3/132 351/221 |
| 6,050,688 A | 4/2000 | Grinblat | |
| 6,319,273 B1 | 11/2001 | Chen et al. | |
| 7,083,281 B2 | 8/2006 | Yogesan et al. | |
| 10,820,797 B2 * | 11/2020 | McWherter ............ | A61B 3/112 |
| 2013/0235346 A1 * | 9/2013 | Huang ................... | A61B 3/152 351/208 |

OTHER PUBLICATIONS

Expert Rev Dermatol. Apr. 1, 2013; 8(2): 177-184. doi:10.1586/edm.13.15., The role of dynamic infrared imaging in melanoma diagnosis, Cila Herman.

\* cited by examiner

*Primary Examiner* — Jie Lei

(74) *Attorney, Agent, or Firm* — Joel Douglas

(57) ABSTRACT

A device and method of ophthalmic diagnosis of lesions on retina utilizing a slit lamp apparatus with a pupil reader and at least one visible LED and one Infrared LED to detect a lesion on the retina of an eye.

20 Claims, 9 Drawing Sheets

DIGITAL 3D INFRARED SLIT LAMP WITH PUPIL MEASUREMENT

CROSS-REFERENCE TO RELATED APPLICATION

This application is a continuation of U.S. patent application Ser. No. 15/981,930, filed May 17, 2018, entitled Digital 3D Infrared Slit lamp with Pupil measurement which is incorporated by reference herein in its entirety. This application claims priority from U.S. provisional patent application Ser. No. 62/636,867, filed Mar. 1, 2018, entitled Digital 3D slit lamp which is hereby incorporated by reference herein for all purposes.

STATEMENT REGARDING FEDERALLY SPONSORED RESEARCH OR DEVELOPMENT

The research for the Patent "Digital 3D Infrared Slit lamp with Pupil measurement" was not funded by any federally sponsored research or development.

DESCRIPTION

Field of Disclosure

This invention relates generally in one aspect to slit lamps for use in ophthalmic diagnosis and treatment. In another aspect, the invention is concerned with the application of a slit lamp to measure metabolic activity with IR light.

Background of the Invention

The cornea of the eye is essential for good vision. It is the outermost tissue of the eye and functions like a window allowing the entry of light into the eye. An established branch of ophthalmic medicine is the examination of optically reflected corneal images as a diagnostic tool in the identification of trachomatous scarring, cataracts, injuries or bacterial and viral infections. These images are captured using slit-lamps to provide a narrow beam of light of elongated slit-shaped cross-section which is projected onto the cornea to study the surface characteristics. The reflected image is in effect an optical section of the anterior part of the eye including the cornea, the anterior chamber, the iris or the lens and the anterior part of the vitreous. For identifying some conditions, the optometrist/ophthalmologist seeks to identify changes in the reflected image over time.

Commercial slit-lamp instruments are generally available and they are used as described to inspect the cornea for various disease states. Additionally, using condensing lenses the retina, a layer of tissue in the back of the eye that collects lights, similar to the film of a camera, can also be evaluated using a slit lamp. It is also known that by changing the wave length of light away from the visible light spectrum and to an infrared light source—a wavelength of light that is poorly absorbed by the retina and eyes photoreceptors, a patient's comfort can be dramatically increased allowing the full field of the patient's fundus to be examined all at one time. Secondly, infrared measuring systems can identify between healthy tissue and a disease state. However, to adequately illuminate the retina the amount of infrared light needs to be tuned to the size of the patient's pupil. This allows the intensity of the infrared light used to be optimized to safely display the greatest thermal imaging response possible between healthy tissue and a disease.

It is an object of this invention to provide a slit-lamp capable of utilizing both visible light and longer wavelength infrared light and allow the physician to alternate the source to get the optimal reading when viewing the cornea and retina of the patient.

It is an object of the invention to provide a slit-lamp capable of measuring critical eye features so that the intensity of the illumination is optimized for the infrared detection cycle and provides an added safety measure to prevent phototoxicity of retina.

It is an object of the invention to provide a slit-lamp capable producing 3D digital images.

BRIEF SUMMARY OF THE INVENTION

In a first aspect, the invention provides slit-lamp apparatus, including a body. Solid state lamp means and associated optics for generating a, narrow beam of light white light and a narrow beam (or full beam) of infrared light and projecting the beams onto the cornea, lens or retina of a patient's eye for reflection by structures of the eye, when the slit-lamp apparatus is position in front of the eye. The solid-state lamp means to detect a reflection of the narrow beam of white light by structures of the eye and to make an image thereof, which image is, or is processable to provide, a digital record of the reflection. The solid-state lamp means being also capable of generating and detecting a narrow beam, or full beam, infrared light by structures of the eye and to make an image thereof, which image is, or is processable to provide, a digital record of the reflection of both the visible and the infrared images. The infrared light is used by the physician to detect any lesions that are on the lens, cornea, retina by looking at the thermal imaging of the eye structures. Additionally, the infrared light intensity is controlled by initial measurements of the Pupil of the eye to ensure the optimal intensity of infrared light is utilized to detect lesions on the, retina or choroid.

For the visible light a narrow beam is preferable in the form of an elongated slit-shaped cross-section. This is due to limitations from reflections from ocular structures but also due to the amount of light that a patient can comfortably tolerate during an examination. For the infrared light source full beam is preferable to illuminate the cornea or retina to achieve a full field view all in one image. The physician is capable of viewing the image from the cornea or retina with a slit lamp and digital imaging.

The solid-state lamp means is conveniently two or more light emitting diodes. At least one LED capable of emitting visible light and another LED being capable of emitting infrared light. Additional, wavelength of lights can also be included in the slit lamp to enhance the evaluation of specific ocular tissue.

Advantageously, the solid-state lamp means consists of a pair of solid-state lamps which have separate controls for activation and intensity.

The associated optics preferably includes a series of lens arranged generally for focusing a light beam emitted towards retina on a patient's eye as a narrow beam of light.

Preferably, the associated optics include structure defining a slit aligned with and disposed to receive light from said elongated light means, to define a light beam of elongated cross-section.

Preferably, there are a pair of said solid state lamp means and associated optics selectively operable for generating and projecting respective said narrow or full beams of light onto the corneas or retina of the patients left and right eyes respectively.

The means to detect the reflection and to make a digital record of the reflection of the narrow beam of light may be a CCD camera but is preferably a digital camera sensor and associated optics.

The slit-lamp apparatus preferably further includes means to transmit the digital record for storage, and for review and diagnosis subsequently and/or at a remote location. Such means to transmit the digital record may comprise WIFI, Bluetooth, USB connection to a local computer for storage and, in one or more embodiments, for online transmission to the remote location.

Preferably, the portable slit-lamp apparatus further includes means mounted to the body for providing background illumination of the cornea and retina. This illumination is preferably of adjustable brightness.

A method is preferably provided as part of the control means for both the visible and infrared light sources to adjust the width, height and orientation of the narrow beam of light.

In a second aspect, the invention provides a method of ophthalmic diagnosis utilizing a slit lamp apparatus according to the first aspect of the invention including: taking a measurement of the Pupil of the patients eye, calculating or selecting an illumination factor based on the Pupil dimension, adjusting the intensity of the light source based on the Pupil size, projecting a narrow or full beam of light, generated by said solid state lamp means and associated optics, onto the cornea or retina of a patient's eye; detecting, with said detecting means, a reflection of said beam of light by structures of the eye, displaying a 3 dimensional image in real time on a display means, making a digital record of the reflection and viewing in real time, and transmitting said digital record to a second location remote from the first for additional review and diagnosis.

Preferably the display means is a comprised of two separate displays that provide a 3D image through 2 separate oculars to achieve stereopsis.

Preferably, said narrow beam is of elongated slit-shaped cross-section.

Preferably, the method further includes reviewing the digital record of the reflections as a 3-dimensional digital image in real time and performing an ophthalmic diagnosis on the basis of the record. Advantageously, the digital record is reproduced as a viewable image/film to assist the physician with the diagnosis.

The transmission of the digital record of the reflection may be by transport of a memory device, but is preferably via the internet or other network means from a local computer at the first location to a remote storage device or computer in a remote site.

BRIEF DESCRIPTION OF THE DRAWINGS

A further understanding of the nature and advantages of embodiments may be realized by reference to the remaining portions of the specification and the drawings, in which like reference numerals are used to refer to similar components. When reference is made to a reference numeral without specification to an existing sub-label, it is intended to refer to all such multiple similar components.

The invention will now be further described by way of example only, with reference to the accompanying drawings, in which.

DETAILED DESCRIPTION OF INVENTION

Figure 1:
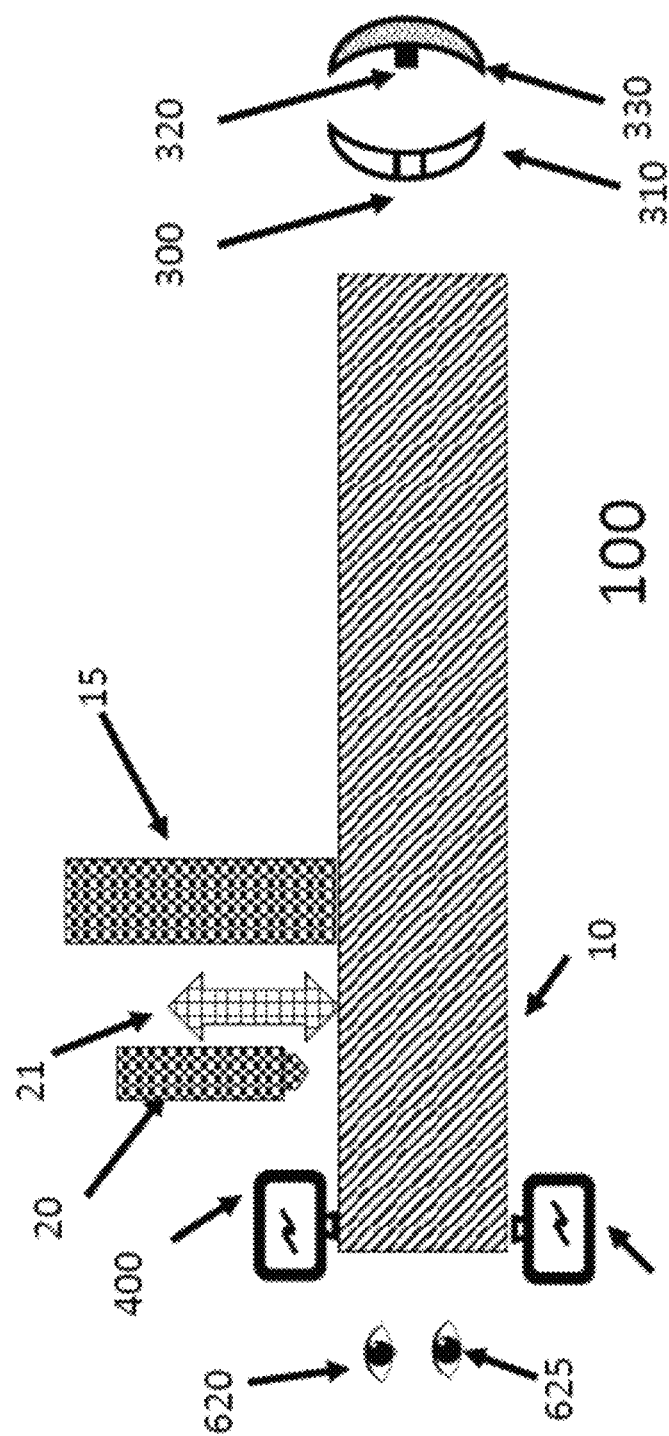
FIG. 1 is a diagram showing the system components of the invention of dual light slit-lamp apparatus and digital monitoring device according to an embodiment of the invention without light paths.

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

In this application the use of the singular includes the plural unless specifically stated otherwise, and use of the terms "and" and "or" is equivalent to "and/or," also referred to as "non-exclusive or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Numerical values for dimensions, volumes and masses in this specification are shown in U.S. customary units. Teaspoons and tablespoons are taken as their volumetric equivalent units in the Avoirdupois system. Since accelerations and forces are not relevant to the description or use of the invention, U.S. customary units of weight such as ounces and pounds shall indicate their customary equivalent masses as stationary objects.

The use of the term physician when used is synonymous with practitioner, nurse, healthcare professional, optician, optometrist, ophthalmologist, technician and person.

The use of the term monitor when used is synonymous with viewing display.

The invention is particularly useful because if not only is applicable for diagnosing lesions on the retina of the eye but can be used to evaluate all the ocular tissue, mostly the cornea, retina, and lens. Therefore. the term ocular tissue can be equally substituted with the term retina, cornea and lens.

The shape and diameter of the human eye after puberty is relatively consistent from patient to patient. The average diameter is of the Pupil is from 1.3 to 8 mm. https://sites.google.com/site/waxfin/eyedimensions. The current practice is to dilate the eye to get the widest aperture. However, this causes discomfort to the patient. Additionally, it has been found that infrared imaging is effective in the diagnosis of melanoma. Published in final edited form as: Expert Rev Dermatol. 2013 Apr. 1; 8(2): 177-184. doi: 10.1586/edm.13.15. This article documented that results from a clinical study suggest that the temperature of cancerous lesions is higher during the first 45-60 seconds of thermal recovery than the temperature of benign pigmented lesions. This small temperature difference can be measured by modern infrared cameras and serve as an indicator for melanoma in modern quantitative melanoma detectors. Therefore, since cancer of the retina is difficult to identify accurately the invention couples the use of thermo-imaging technology with an enhanced ophthalmic slit light device to create a means of inspecting and diagnosing lesions on the retina of the eye. The invention is particularly useful because if not only is applicable for diagnosing lesions on the retina of the eye but can be used to evaluate all the ocular tissue, mostly the cornea, retina, and lens.

The instant invention can best be summarized as a device and method of ophthalmic diagnosis of lesions on retina 330 (the term ocular tissue can be equally substituted with the term cornea and lens) utilizing a slit lamp apparatus 100 as shown in FIGS. 1,2,3,4,5 and 7 with at least one visible LED 120 and one Infrared LED 125 to detect a lesion on the retina 330 of an eye comprising: a) measuring the diameter of the Pupil 300 using a caliper 145 and the light from the infrared LED 125, b) adjusting the intensity of an infrared LED 125 based on the diameter of the Pupil 300, c) applying the infrared light from the infrared LED 125 to the retina 330 of an eye, d) detecting the heat signature of the cells on the retina/ocular tissue 330 using an infrared detector arrays 110 and 115, e) creating a 3D digital image on viewing displays/monitors 400 and 405 from the heat signature on the infrared detector arrays 110 and 115 creating a digital image on viewing displays/monitors 400 and 405, such that the image is viewed through 2 separate oculars to achieve stereopsis f) analyzing the digital image by comparing the difference of the detected heat signature and flagging the higher thermal response for further investigation. g) transmitting said digital image to a computer 1225 for storage, and for review and diagnosis.

Figure 2:
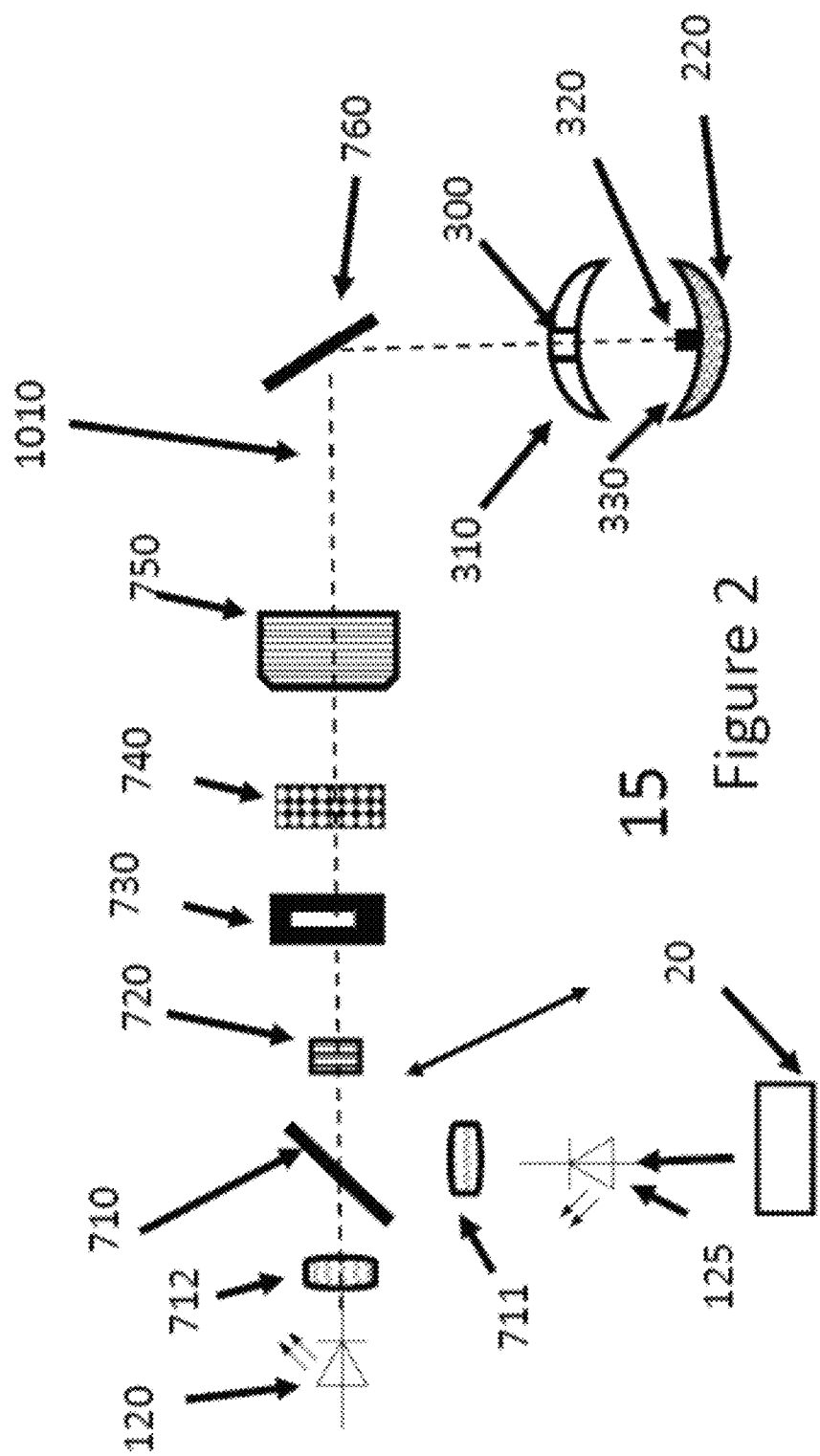
FIG. 2 is a diagram of the light source module showing the light path to the eye.
Figure 3:
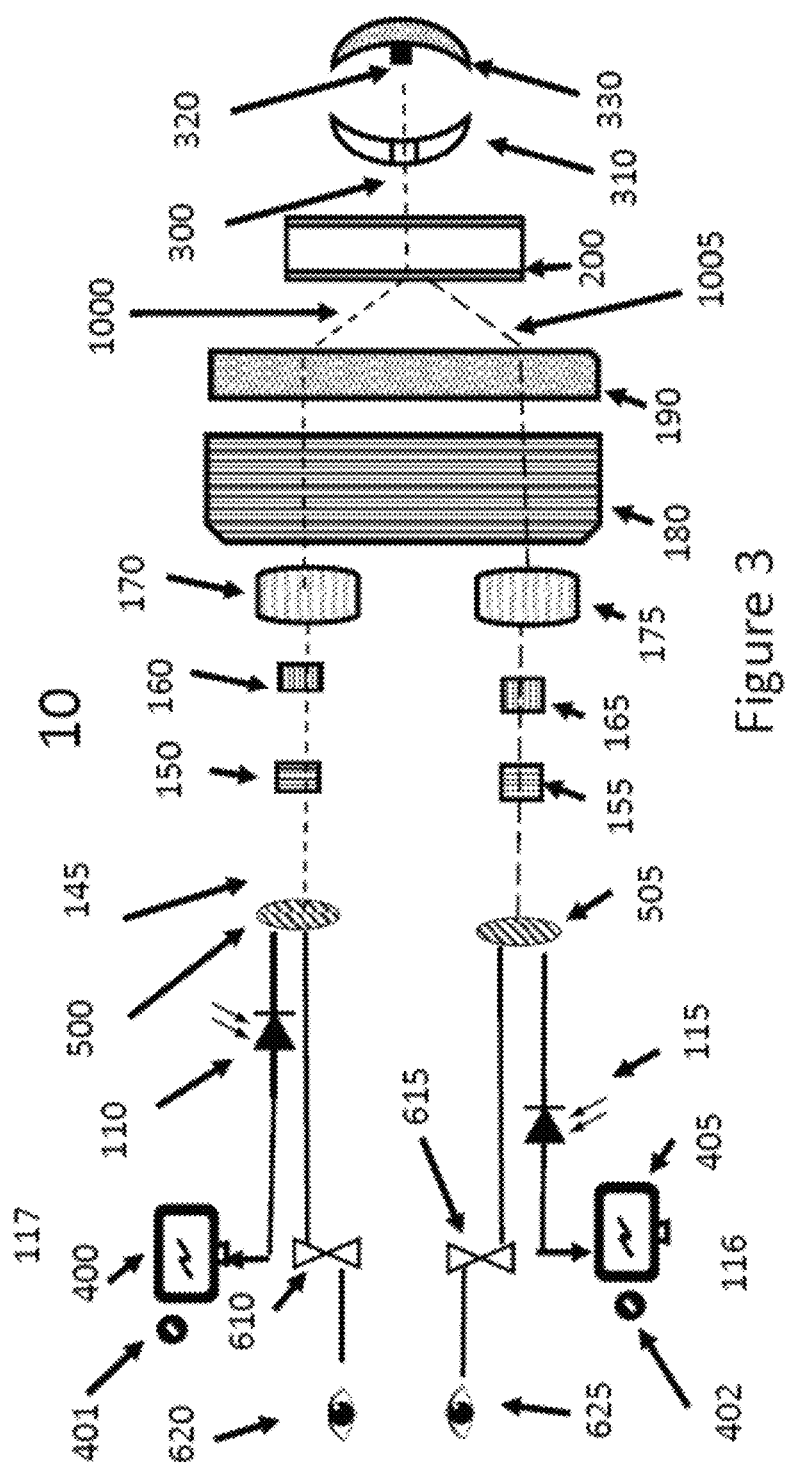
FIG. 3 is a diagram showing the infrared light path from the patient's retina, through the indirect lens, into the stereo slit lamp, ending at the infrared detector arrays for a slit lamp with infrared two detector arrays.
Figure 4:
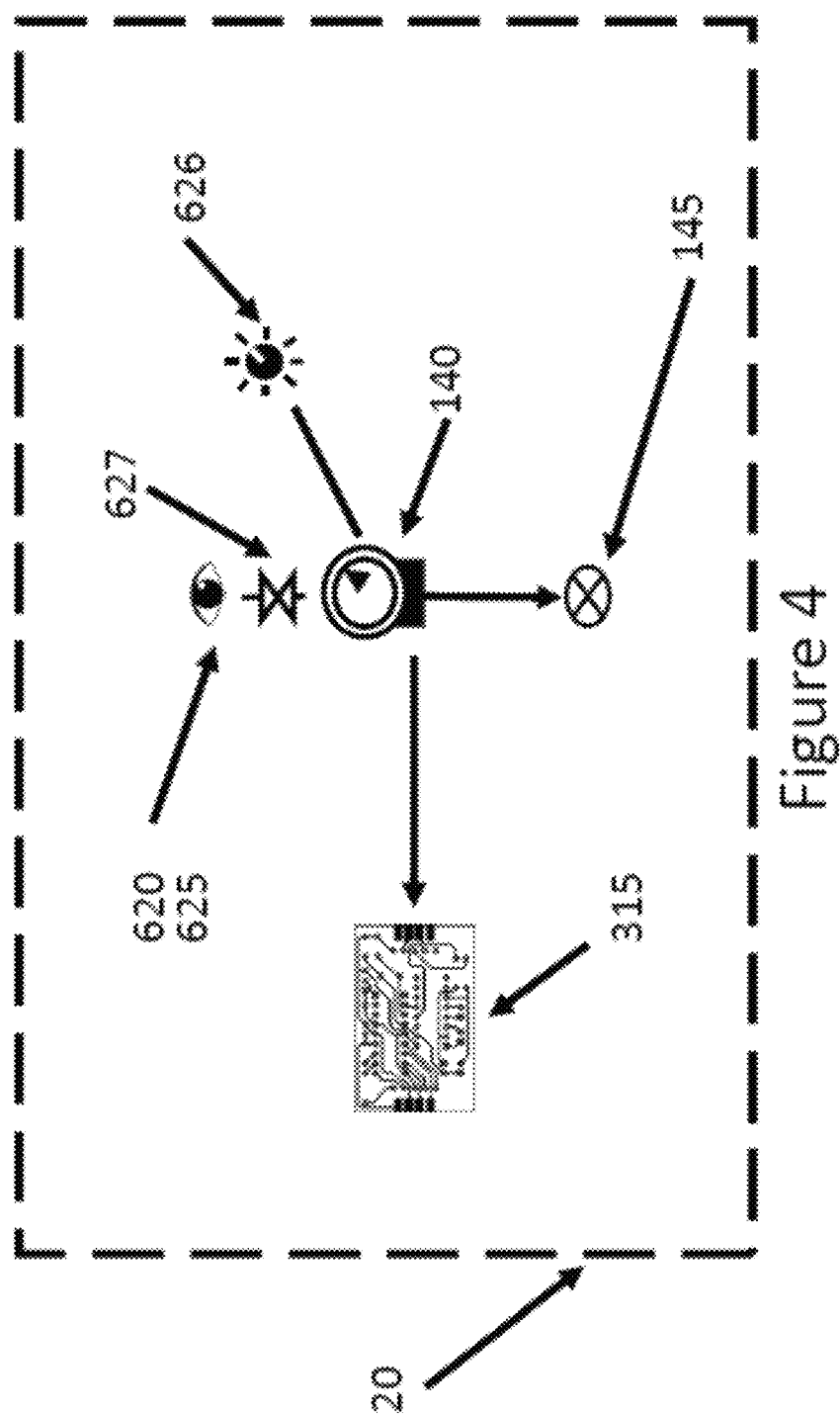
FIG. 4 is a diagram showing the infrared tuning interface system.
Figure 8:
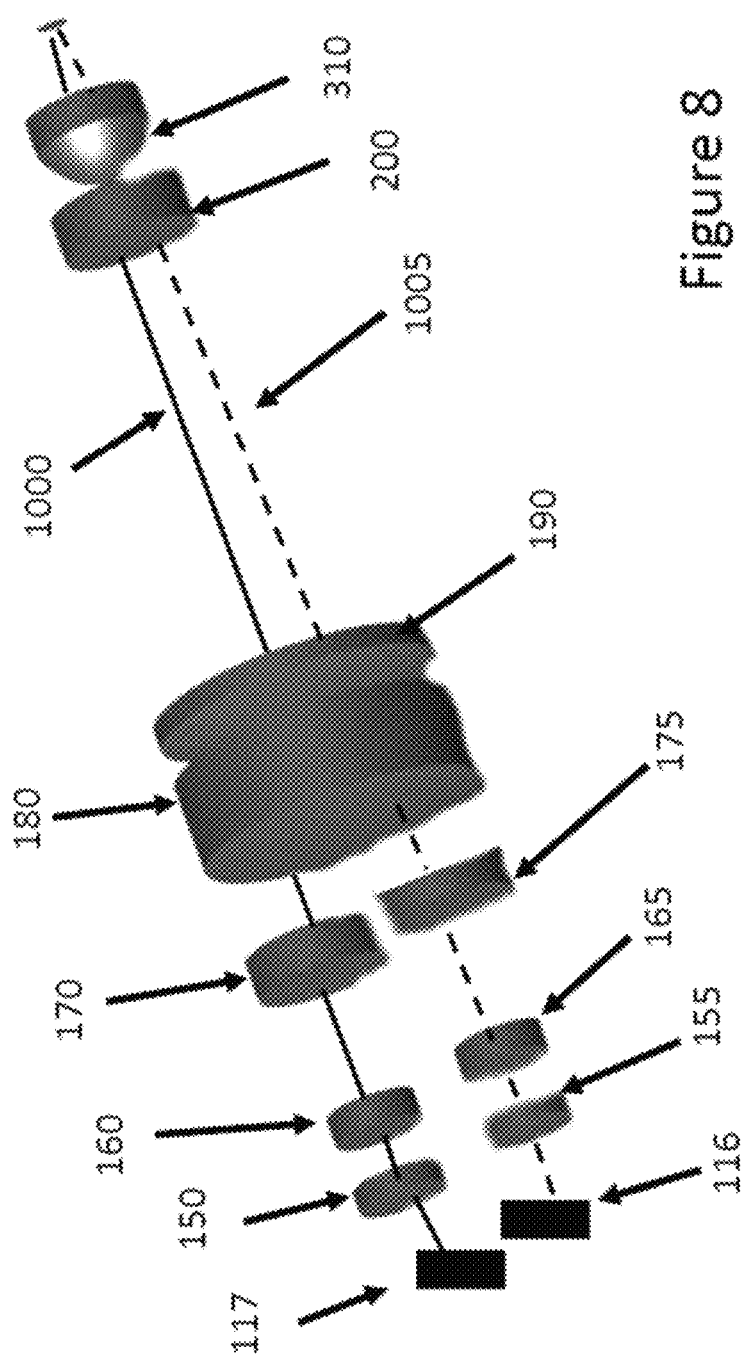
FIG. 8 is a simplified light path diagram of the optics module.

The illustrated slit-lamp apparatus 100 shown graphically in FIGS. 1 and 8 comprises light source 15 optics module 10, Caliper module 20 which is optionally able to be engage or disengage, viewing displays/digital monitors 400 and 405 which form two separate displays that provide a 3D image through 2 separate oculars to achieve stereopsis, a digital link 1224 and computer 1225, and a program to capture the images from said digital monitors. As shown in FIGS. 2 and 4 light source 15 which contains infrared tuning interface 20, which has a Caliper 145 in communication with optics 627. Caliper 145 is also in communication with Pupil reader 140 which uses the infrared light from LED 125 to illuminate the eye 220. The slit-lamp apparatus uses the infrared light from LED 125 to measure the diameter of Pupil 300. The measurement of the diameter of pupil 300 provides the system with the relative opening provided by the Pupil with respect to the eye which permits the controller 315 that is in communication with pupil reader 140 to adjust the intensity of infrared LED 125 so that the intensity of infrared LED 125 provides the best detection parameters to detect a lesion 320 on retina 330. The term retina 330 is used here to provide a tangible organ within the overall structure of the eye. However, the invention is applicable for all ocular tissues and the term retina can be equally substituted with the term ocular tissue, cornea and lens. FIGS. 3 and 8 shows the light paths 1000 and 1005.

As shown in FIGS. 1, 2, 3 and 4 the physician can operate the slit lamp with either visible of infrared light. First reviewing the visible light operation and light path 1010 shown in FIG. 2, the operator first engages the visible light from LED 120 which enters condenser lens 712 and then beam splitter 710. It then enters focusing lens 720 and slit mask 730. It should be noted that the slit mask 730 can also be configured with a means to adjust the width of beam of light from LED 120 or LED 125. The visible light from LED 120 then enters the color filter 740 and the projection lens filter 750. The light proceeds mirror 760 and onto to eye 220 passing through and illuminating the retina 330. The light from the infrared LED 120 is then reflected to the viewing display/monitors 400 and 405, which form two separate displays that provide a 3D image through 2 separate oculars to achieve stereopsis, or are visually observed by the operator using separate oculars using eyes 620 or 625 using the necessary protective eyewear. As shown in FIGS. 3 and 4 the light reflected off retina 330 to get to the viewing display/monitors 400 and 405 or are visually observed by the operator using eyes 620 Or 625 must first pass through most distal lens indirect lens 200 which splits the reflected light into light path 1000 and 1005 then the respective focusing and combining optics module formed from Lens 190 and 180. The light then passes through the zoom lens module which consist of lenses 175, 170, 160,165, 155, 150. When the light exits the most proximal lens pair and 150 and 155 it enters the splitter 500 or 505 which splits the light paths 1000 and 1005 respectively so that it can take two different paths. The first path the light is transmitted to the detection array assembly 117 comprising of detector array 110 and viewing display/monitor 400 or detection array assembly 116 comprising of detector arrays 110 and 115 and viewing display/monitor 405. The physician can view the images on viewing displays/monitors 400 and 405 which form two separate displays that provide a 3D image through 2 separate oculars to achieve stereopsis.

Figure 7:
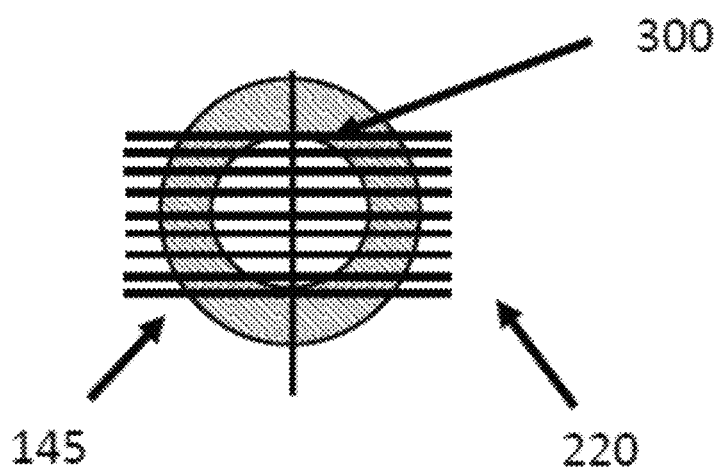
FIG. 7 is a diagram showing the patients pupil and the caliper for measuring the pupil.

If the physician wants to inspect the ocular tissue 310 using infrared light the physician must first measure the pupil to determine the correct intensity settings for the infrared light LED 125. To do this the operator first engages the Caliper module 20. Caliper module 20 is preferably engaged by slide 21 by sliding Caliper module 20 into optics module 10. However, the Caliper module 20 could be installed in a non-moveable embodiment if the optics were arranged so that the light would on be obstructed by the Caliper 146. Once the Caliper module 20 is in place the physician then engages the infrared light from LED 125 which transmits the infrared light so that it enters condenser lens 711 and then beam splitter 710. After entering the beam splitter 710 the infrared light is on light path 1010. The infrared light then enters focusing lens 720 and slit mask 730. It should be noted that the slit mask 730 can also be configured with a means to adjust the width of beam of light from LED 120 or LED 125. The infrared light from LED 125 then enters the color filter 740 and the projection lens filter 750. The light proceeds mirror 760 and onto to eye 220 passing through and illuminating the retina 330. The infrared light from LED 125 is then reflected off retina 330 tin the direction of the viewing display/monitor 400 and 405. Once the light is reflected off retina 330 the infrared light must first pass through most distal lens indirect lens 200 where it is split into infrared light path 1000 and 1005. The infrared light then travels through focusing and combining optics module formed from Lens 190 and 180. The infrared light then passes through the zoom lens module which consist of lenses 175, 170, 160,165, 155, 150. When the light exits the most proximal lens pair and 150 and 155 it enters Caliper module 20. The operator uses the Caliper module 20 as shown in FIGS. 1, 4 and 7 to measure the pupil diameter which uses Caliper 145, pupil reader 140, optics 627. The operator accomplishes this by measuring the pupil diameter by viewing the pupil with either eye 620 or 625 using optics 627 and using the necessary protective eyewear and using Caliper 145 to determine the diameter of the pupil. The operator then adjusts tuning control 626 to provide the pupil diameter to infrared LED controller 315 which adjust the intensity of the power driving infrared LED 125. Alternatively, Pupil reader 140 can be designed so that it automatically takes the pupil reading by finding the two most distal points of the interior dimension of the pupil and then bypass tuning control 626 and sets the pupil parameter automatically without intervention from the physician. As the reader is aware the infrared radiation extends from the nominal red edge of the visible spectrum at 700 nanometers (nm) to 1 millimeter (mm). Preferably, the infrared wavelength of the invention's LED 125 is 940-950 nm. However, from initial testing different wavelengths may increase the ability of the invention to identify lesions on the retina. As shown in FIG. 7 when the invention is used without an automated Pupil reader 140 the patients eye 220 and Pupil 300 is seen with the caliper 145 displayed over the Pupil. The physician counts the indicator marks and each indicator mark is equal to 1 mm of Pupil exposure. The physician would set the tuning control 626 to 9 for 9 MM which would reduce the intensity of the infrared light due to the increase area of light entering the eye through Pupil 300 and making contact with the on retina 330. Preferably, a 9 setting on tuning control 626 is equivalent to a 4 percent reduction in intensity delivered to the LED 125 by infrared LED controller 315. Also, preferably, each mm reduction in diameter of the pupil as measured by the Caliper 145 represents an additional 0.376% in intensity delivered to the LED 125 by infrared LED controller 315. Therefore, an 8 mm diameter pupil would result in a 3.624% decrease in the intensity delivered to the LED 125 by infrared LED controller 315 and a 1 mm diameter pupil would result in full intensity of the LED 125 being applied to the retina 330. This can be automated by integrating the necessary controls into pupil reader 140 such that the pupil reader 140 automatically takes the pupil reading by finding the two most distal points of the interior dimension of the pupil and then by passing tuning control 626 and to set the pupil parameter automatically without intervention from the physician. The change of intensity to the LED 125 is achieved by integrating pulse width modulation into the control circuit for the infrared LED controller 315, With pulse width modulation, less power is wasted because the drive transistors utilized to achieve the pulse width modulation are either on or off, and when on they have a very low resistance. The circuit needs have a resistor to limit the current when turned on. The design can also incorporate an optional DC to DC converter to generate the correct drive voltage from the input voltage. The required frequency is preferable in the 1 kHz or higher range to limit visible flickering.

Figure 9:
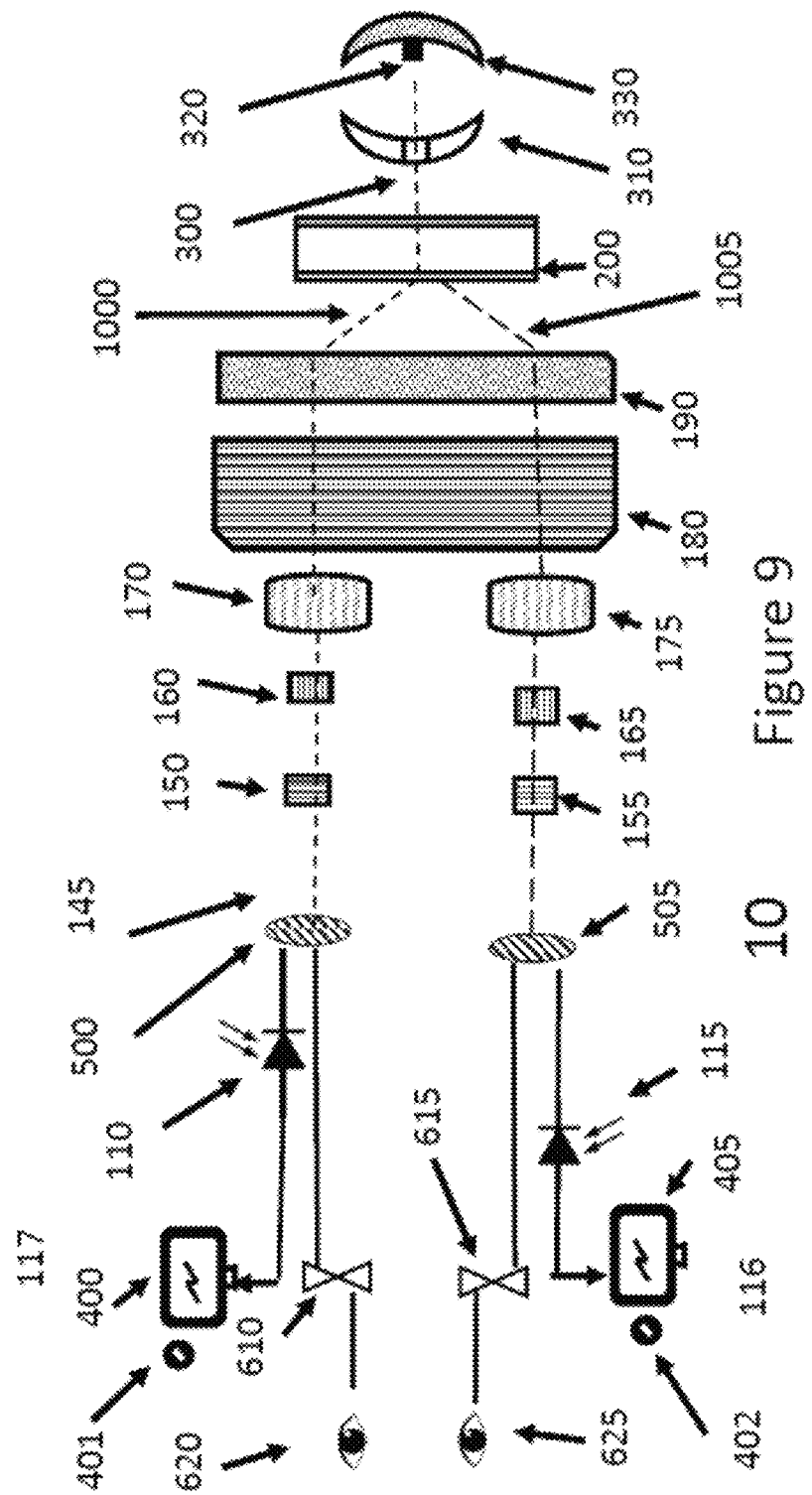
FIG. 9 shows the light path of the optics module without Caliper module in the light path

Once the intensity for the infrared LED 125 has been adjusted the physician must first disengage the Caliper module 20 by slide 21. See FIG. 9 for the light path without Caliper module 20 in the light path. The next step is to turn on infrared LED 125 and insure that the visible light LED 120 is off. To make this more automated an interlock system can be implemented that would not allow the visible LED 120 to be on when infrared LED 125 is on. For the operator to see the lesion 320 the infrared light from LED 125 must be applied to the retina 330 or other ocular tissue 310 and therefore must take the following path to the retina. The light from infrared LED 125 enters condenser lens 711 and then beam splitter 710. It then enters focusing lens 720 and slit mask 730. The visible light from LED 120 then enters the color filter 740 and the projection lens filter 750. The light proceeds to mirror 760 and to patient's eye 220 passing through Pupil 300 and illuminating retina 330. The light from the infrared LED 125 is then reflected to the viewing display/monitor 400 and 405 which form two separate displays that provide a 3D image through 2 separate oculars to achieve stereopsis, or are visually observed by the operator using eyes 620 or 625 using the necessary protective eyewear, this path also provides 2 separate oculars to achieve stereopsis. As shown in FIGS. 2 and 3 the light reflected off retina 330 to get to the viewing display/monitor 400 and 405 or are visually observed by the operator using eyes 620 or 625 must first pass through most distal lens indirect lens 200 then the focusing and combining optics module formed from Lens 190 and 180. The light then passes through the zoom lens module which consist of lenses 175, 170, 160,165, 155, 150. The light exits the most proximal lens pair and 150 and 155 and since the Caliper module 20 is disengaged from the light path the light enters the splitter 500 or 505 which splits the light so that it can take two different paths. The first path the light is transmitted through double porroprisms 610 and double porroprisms 615 respectively and image is visible through 2 separate oculars to achieve stereopsis. If required by manufacturing the prisms can be omitted. The second path the light is transmitted to the infrared detection array assembly 117 comprising of infrared detector array 110 and viewing display/monitor 400 or detection array assembly 116 comprising of detector arrays 115 and viewing display/monitor 405. Viewing display/monitors 400 and 405 form two separate displays that provide a 3D image through 2 separate oculars to achieve stereopsis. The infrared detector arrays 110 and 115 is preferably, a Hamamatsu G11478-256WB which has proven to perform well when integrated into the invention. However, many different sensors could be utilized and the sensor selected being dependent on the electronics utilized to detect and process the signal. Alternatively, the detection array can be a CCD camera and associated optics adapted for thermal imaging. The viewing displays/monitors 400 and 405 provide the physician the ability to look at the infrared image of the retina or other ocular tissue to identify areas which have a higher heat signature and therefore identify the areas of concern which can then be evaluated by traditional techniques. The viewing displays/monitors 400 and 405 form two separate displays that provide a 3D image through 2 separate oculars to achieve stereopsis. The invention can utilize a number of different monitors which are capable of receiving and processing the infrared information from the infrared detector arrays 110 and 115. The utility of the invention is based on the findings that the temperature of cancerous lesions is higher during the first 45-60 seconds of thermal recovery when subjected to infrared radiation than the temperature of benign lesions. This small temperature difference can be measured and serves as an indicator for cancer in the cells of the retina and other ocular tissue. Therefore, by detecting the heat signature of the cells on the retina and comparing the difference of the detected heat signature and flagging the higher thermal response the physician can determine which cells need to be further evaluated and the difference in readings serves as an indicator that the cells may be cancer. The system could also be automated to provide an algorithm that analyzes the heat detected from the ocular tissue and then provide a summary 3-dimensional view of the ocular tissue being examined.

Figure 6:
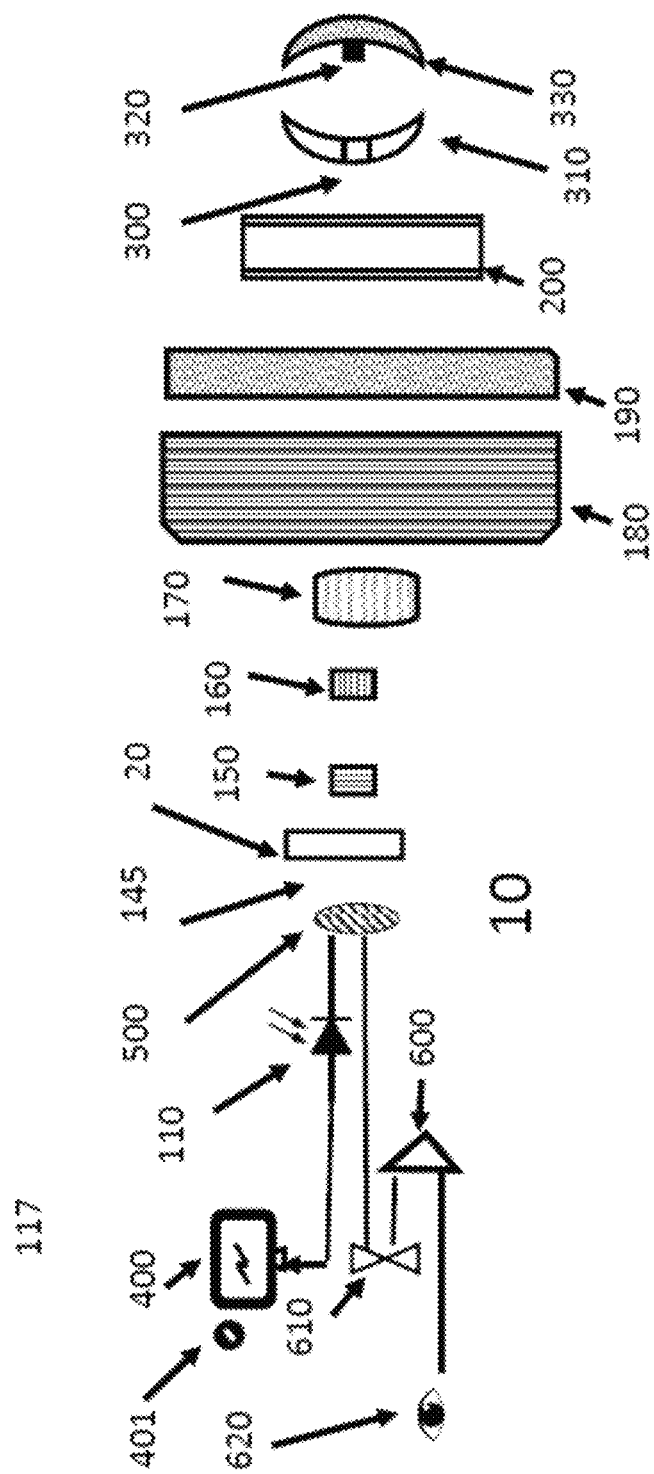
FIG. 6 is a diagram showing the infrared light path from the patient's retina, through the indirect lens, into the mono slit lamp, ending at the infrared detector array for a slit lamp with infrared one detector array.

The preferred embodiment of the invention has two parallel optic module light paths and digital monitors. However, the invention in an alternative embodiment could have one digital monitor and corresponding light path. The single light path embodiment is represented in FIG. 6 and for the operator to see the lesion 320 the infrared light from LED 125 must be applied to the retina and therefore must take the similar path as the two-light path embodiment and must first pass through most distal lens indirect lens 200 then the focusing and combining optics module formed from Lens 190 and 180. The light then passes through the zoom lens module which consist of lenses 170, 160 and 150. When the light exits the most proximal lens 150 it enters the splitter 500 which splits the light so that it can take two different paths. The first path the light is transmitted to the infrared detection array assembly 117 comprising of infrared detector array 110 and viewing display/monitor 400. The viewing display/monitor 400 can provide the physician the ability to look at the infrared image of the retina to identify areas which have a higher heat signature and therefore identify the areas of concern which can then be evaluated by traditional techniques. By detecting the heat signature of the cells on the retina the physician can determine which cells need to be further evaluated and the difference in readings serves as an indicator for cancer in the cells of the retina.

It should be noted that the images on viewing displays/monitors 400 and 405 of the Slit-lamp of the invention may be at a fixed angle as illustrated, or mounted for pivotal adjustment to different angles. Magnification may also be variable.

Figure 5:
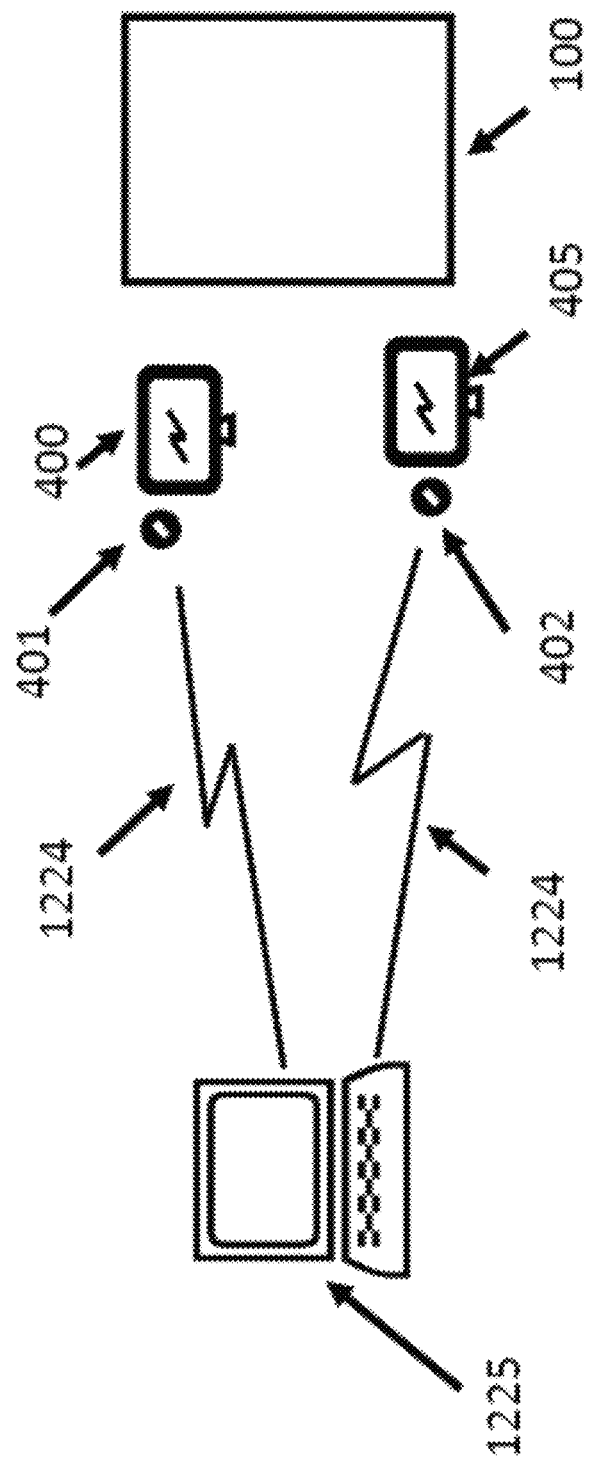
FIG. 5 is a diagram of the invention used with an associated computer system.

The camera image is viewed in real time on a rear-facing viewing displays/monitors 400 and 405. The viewing displays/monitors 400 and 405 in the preferred embodiment are adjustable of an angular orientation. When it is desired to capture and store an image, as shown in FIG. 5 the physician triggers image capture by activating either button 401 or 402 and the captured image is transmitted by a transmission means as a digital record to a local computer 1225. The transmission means being selected from the Bluetooth, WIFI, USB connection or a cable link 1224. The local computer 1225 may also be configured such that it is a remote device in another room or office or building.

When the physician of the slit lamp presses button 401 or 402, the software program residing on the computer 1225 detects the signals and grab images and stores them on the computer. Therefore, a particular image or video clip can be selected for saving on file in the computer. In an alternative embodiment, the instrument may store digital image records on a memory card that can be downloaded to the computer.

Alternatively, the LEDs 120 and 125 also can comprises one or more light emitting diodes to form an LED array, It will be appreciated that the illustrated instrument has the great practical advantage in that the capture slit-lamp images can be stored in digital format in a computer hard disk or other storage device for transfer to another location for subsequent diagnosis by optometrist/ophthalmologists or other skilled professionals. In accordance with a preferred aspect of the invention, however, the digital record of the images may be transmitted online, via the internet or other network means, to the other location for review and diagnosis. The diagnosis may then be transmitted or forwarded back, e.g. as an online response to the forwarder of the image.

While certain features and aspects have been described with respect to exemplary embodiments, one skilled in the art will recognize that numerous modifications are possible. Further, while various methods and processes described herein may be described with respect to particular structural and/or functional components for ease of description, methods provided by various embodiments are not limited to any particular structural and/or functional architecture.

Hence, while various embodiments are described with or without certain features for ease of description and to illustrate exemplary aspects of those embodiments, the various components and/or features described herein with respect to a particular embodiment can be substituted, added, and/or subtracted from among other described embodiments, unless the context dictates otherwise. Consequently, although several exemplary embodiments are described above, it will be appreciated that the invention is intended to cover all modifications and equivalents within the scope of the following claims.

I claim:

1. A method of using a slit-lamp apparatus to detect a lesion on the ocular tissue of a patient's eye wherein said slit-lamp apparatus comprising of a light source module comprising of at least one visible LED capable of emitting visible LED light and at least one Infrared LED capable of emitting Infrared LED light, an optics module and said optics module is in communication with a caliper module and digital monitors, and said digital monitors has a digital link to a computer and a program on said computer to capture the images from said digital monitors and said caliper module having a pupil reader and said pupil reader capable of measuring the area of light that actually falls on the retina of the patient's eye and said caliper module displays on said digital monitors an intensity setting of said infrared LED in said light source module using said digital monitors and said intensity setting of said infrared LED is based on the area of light that actually falls on the retina of the patient's eye and said light source module automatically sends intensity of said infrared LED to an infrared LED controller and said infrared LED light is projected onto the ocular tissue of said patient's eye and said infrared LED light is capable of producing a heat signature of the cells on said ocular tissue of a patient's eye;

a) said digital monitors detects said heat signature of the cells on said ocular tissue of a patient's eye resulting from said infrared LED using an infrared detection array, b) said slit-lamp apparatus creates a 3-dimensional digital image on said digital monitors from said heat signature on said infrared detection array using said optics module, c) said slit-lamp apparatus analyzing the said digital image by comparing the difference of the detected heat signature and flagging higher thermal response investigation by said physician, d) said slit-lamp apparatus transmitting said digital image on said viewing displays to a computer for storage using a transmission means, for review and diagnosis by said physician.

2. The infrared LED controller of claim 1 wherein comprises of a tuning control device to adjust the intensity of the power to said infrared LED.

3. The digital monitors of claim 1 wherein said digital monitors is a CCD camera and associated optics adapted for thermal imaging.

4. The computer of claim 1 comprising of a processor and a program to receive images from said digital monitors and said digital monitors are in communication with said computer by a communication link.

5. The optics module of claim 1, wherein said optics module comprises of an indirect lens distal from said digital monitors, a focusing lens, a combining optics module, a zoom lens module, a splitter lens, an at least one infrared detection array assembly.

6. The communication link of claim 1, wherein and said communication link consisting of Bluetooth, WIFI, USB connection and a cable link.

7. The ocular tissue of claim 1, wherein the ocular tissue is selected from the group consisting of lens, retina and cornea.

8. A method of using a slit-lamp apparatus to detect a lesion on the ocular tissue of a patient's eye wherein said slit-lamp apparatus comprising of a light source module comprising of at least one visible LED capable of emitting visible LED light and at least one Infrared LED capable of emitting Infrared LED light, an optics module and said optics module is in communication with a caliper module and digital monitors, and said digital monitors has a digital link to a computer and a program on said computer to capture the images from said digital monitors and said caliper module having a pupil reader and said pupil reader capable of measuring the area of light that actually falls on the retina of the patient's eye and said caliper module determines an intensity setting for said infrared LED based on measuring the area of light that actually falls on the retina of the patient's eye and displays on said digital monitors the intensity setting of said infrared LED in said light source module using said digital monitors and said intensity of said infrared LED in said light source module and said intensity setting of said infrared LED is automatically sent to an infrared LED controller and said infrared LED light is projected onto the ocular tissue of said patient's eye and said infrared LED light is capable of producing a heat signature of the cells on said ocular tissue of a patient's eye:
  a) said digital monitors detects said heat signature of the cells on said ocular tissue of a patient's eye resulting from said infrared LED using an infrared detection array,
  b) said slit-lamp apparatus creates a 3-dimensional digital image on said digital monitors from said heat signature on said infrared detection array using said optics module,
  c) said slit-lamp apparatus analyzing the said digital image by comparing the difference of the detected heat signature and flagging higher thermal response for investigation by said physician,
  d) said physician using said digital image on said viewing displays for review and diagnosis by said physician and said physician storing said digital image on said viewing display to a computer for storage using a transmission means.

9. The infrared LED controller of claim 8 wherein comprises of a tuning control device to adjust the intensity of the power to said infrared LED.

10. The digital monitors of claim 8 wherein said digital monitors is a CCD camera and associated optics adapted for thermal imaging.

11. The computer of claim 8 comprising of a processor and a program to receive images from said digital monitors and said digital monitors are in communication with said computer by a communication link.

12. The optics module of claim 8, wherein said optics module comprises of an indirect lens distal from said digital monitors, a focusing lens, a combining optics module, a zoom lens module, a splitter lens, an at least one infrared detection array assembly.

13. The communication link of claim 8, wherein and said communication link consisting of Bluetooth, WIFI, USB connection and a cable link.

14. The ocular tissue of claim 8, wherein the ocular tissue is selected from the group consisting of lens, retina and cornea.

15. A method of ophthalmic diagnosis by a physician utilizing a slit lamp apparatus to detect a lesion on the ocular tissue of an eye comprising:
  a) physician measuring the diameter of the pupil using a caliper module and said caliper module having a pupil reader and said pupil reader capable of measuring the area of light that actually falls on the retina of the patient's eye and said caliper module displays on said digital monitors an intensity setting of the infrared LED in said light source module using said digital monitors and said intensity setting of said infrared LED is based on the area of light that actually falls on the retina of the patient's eye
  b) adjusting the intensity of said infrared LED based on the area of light that actually falls on the retina of the patient's eye;
  c) applying the infrared light from said infrared LED to the ocular tissue of an eye,
  d) detecting the heat signature of the cells on said ocular tissue using an infrared detection array;
  e) creating a 3-dimensional digital image on viewing displays from said heat signature on said infrared detection array;
  f) analyzing the said digital image by comparing the difference of the detected heat signature and flagging higher thermal response for further investigation by said physician;
  g) transmitting said digital image on said viewing displays to a computer for storage using a transmission means, and for review and diagnosis.

16. The ocular tissue of claim 15, wherein the ocular tissue is selected from the group consisting of lens, retina and cornea.

17. The transmission means of claim 15, wherein the transmission means is selected from the group consisting of Bluetooth, WIFI, USB connection and a cable link.

18. A method according to claim 15, further including reproducing said digital image as a viewable image.

19. A method according to claim 15, further including analyzing the digital image and performing an ophthalmic diagnosis on the basis of the record.

20. A method according to claim 15, where said transmission of the digital image wherein said digital monitor are in communication with said computer by a communication link and said communication link consisting of Bluetooth, WIFI, USB connection and a cable link.

* * * * *